United States Patent [19]

Hugl et al.

[11] Patent Number: 5,030,697

[45] Date of Patent: Jul. 9, 1991

[54] POLYMER-BOUND DYES, PROCESS FOR THEIR PRODUCTION AND USE

[75] Inventors: Herbert Hugl; Bruno Bömer, both of Bergisch-Gladbach, Fed. Rep. of Germany; Heinz Kölbl, West Haven, Conn.; Florin Seng, Bergisch-Gladbach, Fed. Rep. of Germany; Eberhard Kuckert, West Haven, Conn.; Günter Sackmann, Leverkusen, Fed. Rep. of Germany

[73] Assignee: Bayer Aktiengesellschaft, Leverkusen, Fed. Rep. of Germany

[21] Appl. No.: 408,858

[22] Filed: Sep. 18, 1989

[30] Foreign Application Priority Data

Sep. 28, 1988 [DE] Fed. Rep. of Germany ....... 3832830
Jun. 30, 1989 [DE] Fed. Rep. of Germany ....... 3921498

[51] Int. Cl.$^5$ ................................................ C08F 8/32
[52] U.S. Cl. ............................. 525/326.9; 525/328.2; 525/328.9; 525/329.4; 525/333.7; 525/375; 525/376; 525/380
[58] Field of Search ............... 525/326.9, 328.2, 328.9, 525/329.4, 333.7

[56] References Cited

U.S. PATENT DOCUMENTS 4,166,105 8/1979 Hirschfeld .

Primary Examiner—Bernard Lipman
Attorney, Agent, or Firm—Sprung Horn Kramer & Woods

[57] ABSTRACT

A polymer-bound linkable dye comprising
a) a water-soluble polymer backbone,
b) a dye covalently bound thereto, and
c) functional groups which enable the polymer-dye to link covalently with biological materials, in which the water-soluble polymer backbone is a copolymer which contains arcylamide, methacrylamide, N-$C_1$-$C_4$alkyl(meth)acrylamide, N,N-$C_1$-$C_4$dialkylacrylamide, N-vinylpyrrolidone, N-vinylpiperidone, N-vinylcaprolactam, N-vinylformamide, N-vinylacetamide, N-vinyl-N-methylacetamide, N-vinyl-O-methylurethane, ethene or vinylmethylether as nonionic monomer blocks. The polymer-bound dye can be linked to a biologically active material such as an antibody or nucleic acid and used analytically.

6 Claims, No Drawings

POLYMER-BOUND DYES, PROCESS FOR THEIR PRODUCTION AND USE

The present invention related to polymer-bound dyes, a process for their production and their use for example as marker substances in analytical procedures. The polymer-bound dyes, also called polymer dyes, contain linkable functional groups and are water-soluble under normal analytical conditions. This water solubility is normally due to the polymer component. The dyes themselves are often insoluble in water.

The object on which the present invention was based, was to develop new marker substances which can be used in biological test systems The marker substances should have a sensitivity to detection comparable with the known marker substances. They should not have the disadvantages of the latter however, such as for example low safety in use and use being possible only in special laboratories (radioactivity) or inadequate stability (enzyme marking).

The polymer dyes according to the invention normally have an average molecular on weight on the order of magnitude of about $\overline{M}_n = 2 \times 10^3$ to about $5 \times 10^6$ Dalton. Molecular weights of about $10^4$ to $10^5$ Dalton are preferred.

Under normal analytical conditions the polymer dyes are soluble in aqueous media to at least 0.1%, preferably at least to 1%.

Normal analytical conditions are understood to mean those prevalent in biological tests, particularly in binding methods of analysis, such as for example immunoassays or gene-probe tests. Here, for example, temperatures of up to about 70° C., preferably of about 10° C. to 40° C. and pH values of about 3 to 11, preferably of 5 to 9, may be mentioned. In special tests or analytical procedures it is certainly possible to depart from these values. The water solubility of the polymer-bound dyes is vital, because due to this the use of the dyes is possible in biological analytical procedures.

Colored polymers and their production by reacting polymers containing dicarboxylic anhydride groups with, preferably, dyes containing amino groups are known. For example in US-PS 3 915 635 Kalopissis and Viout describe a hair treatment product containing polymer dyes produced from polymers containing anhydride groups and azo, anthraquinone or benzene dyes with amino groups. These polymers are, however, only soluble in aqueous alcohols and not in water. What is more, they do not have any additional reactive groups which enable controlled bonding with, e.g., antibodies or DNA.

In U.S. Pat. No. 4,166,105 Hirschfeld describes reagents for the detection of specific reactants such as antigens, which comprise polymers bound to an antibody containing a large number of dye molecules. The dye polymers have functional end groups used for bonding protein, and many other functional groups used for bonding dye molecules. Polyethylene imines, polylysine and polyamides such as Nylon 6, and low-molecular polycarboxylic acids are named as suitable backbone polymers.

The first example in such patent describes the synthesis of a polymer dye from polyethylene imine and fluorescein isothiocyanate, which contains 70 dyestuff molecules per molecule of polyethylene imine. In Example 7, however, the quantum yield of a polymer dye with 80 bound fluorescein units is determined to be just 4%. This shows that at around one hundred times the molecular weight the fluorescence of this polymer is only about three times as strong as that of monomer FITC.

By contrast, the present invention shows that by bonding 4-amino fluorescein to acrylamide maleic anhydride copolymers, polymer dyes with strong fluorescence and quantum yields of over 60% are obtained.

The polymer dyes according to the invention consist of a water-soluble polymer backbone, to which suitable dyes are covalently bound via spacers and which moreover contains other functional groups which enable the polymer dye to be covalently linked with biological materials such as for example with proteins or functional oligonucleotides.

Functional groups suitable for this purpose are for example hydroxyl, amino, carboxyl or also thio groups and isothiocyanato groups, additionally N-hydroxysuccinimide ester groups, N-hydroxyphthalimide ester groups or N-acylbenzotriazole groups and also in the case where a linkage is possible under particularly gentle, preferably dry conditions, acid chloride, acid anhydride and isocyanate groups.

The polymers consist of covalently linked (copolymerized) monomer building blocks, which lend the advantageous properties to the polymer.

1. Water solubility-promoting nonionic monomer building blocks such as acrylamide, methacrylamide, N-$C_1$-$C_4$ alkyl(meth)acrylamides, N,N-$C_1$-$C_4$dialkylacrylamides, N-vinylpyrrolidone, N-vinylpiperidone, N-vinylcaprolactam, N-vinylformamide, N-vinylacetamide, N-vinyl-N-methylacetamide, N-vinyl-O-methylurethane.

2. Dye molecules covalently bound via ester groups or acid imide groups or preferably acid amide groups.

The dye molecules can be introduced either by copolymerization of relevant dye monomers such as (meth)acrylic esters of suitable dyes or (meth)acrylamides of suitable dyes or by reacting dyes which preferably contain amino groups with reactive groups of the backbone polymer.

Monomers which introduce reactive groups are for example maleic anhydride, itaconic anhydride, citraconic anhydride, (meth)acryloyl chloride, N-hydroxysuccinimide (meth)acrylate, N-hydroxyphthalimide (meth)acrylate, N-(meth)acryloylbenzotriazole, 3- or 4-isothiocyanatophenyl (meth)acrylate, 2-isocyanatoethyl methacrylate, isocyanatostyrene, isocyanatoisopropenylbenzene, vinyloxirane as well as (meth)acrylic acid in combination with carbodiimides.

3. Monomer building blocks containing reactive groups or groups which can be activated, which enable a covalent linkage to be formed for example with the antibodies antigens, haptens or nucleic acids and optionally with the dye molecules.

This function can be carried out by the monomers mentioned above which introduce reactive groups, if they have not been reacted quantitatively with dye molecules and if the linkage can be carried out under conditions such that hydrolysis of the reactive groups is negligible.

Moreover, for this purpose, monomers containing an aliphatic alcohol group such as hydroxyalkyl (meth)acrylates such as hydroxyethyl (meth)acrylate, hydroxypropyl (meth)acrylate, and butanediol mono(meth)acrylate can preferably be incorporated, The alcohol group can also be introduced by reacting the reactive groups mentioned under 2. of the backbone polymer with aminoalcohols such as aminoethanol, aminopropanol or 6-amino-1-hexanol.

The alcohol group of the polymer is activated by conversion to the tresyl group (=trifluoromethanesulphonyl group) or the methanesulphonyl group.

4. If desired, ionic monomer building blocks which increase the water solubility of the polymer such as (meth)acrylic acid, 2-acryloylamino-2-methylpropanesulphonic acid, styrenesulphonic acid, dialkylaminoalkyl (meth)acrylates or dialkylaminoalkyl(meth)acrylamides such as dimethylaminoethyl methacrylate or dimethylaminopropylacrylamide or the quaternized (meth)acrylates or (meth)acrylamides derived from these monomers can be copolymerized.

Moreover, additional carboxyl, sulphonic acid or tert-amino groups can be introduced by reacting a part of the reactive groups of the backbone polymer with amino carboxylic acids, aminosulphonic acids or primary-tertiary or secondary-tertiary diamines.

The incorporation of ionic groups is particularly preferred, when the polymers contain a high proportion of hydrophobic dye molecules.

The preferred linkable anionic polymer dyes have the general formula:

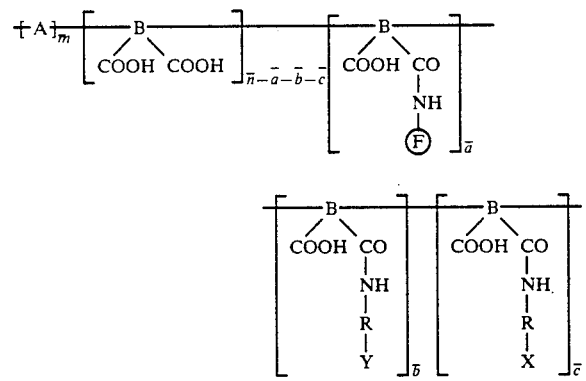

A = monomers which can be copolymerized with unsaturated dicarboxylic anhydrides, for example acrylamide, methacrylamide, N-$C_1$-$C_4$-alkyl(meth)acrylamides, N,N-$C_1$-$C_4$-dialkylacrrylamides, N-vinylpyrrolidone, N-vinylpiperidone, N-vinyl-caprolactam, N-vinylformamide, N-vinylacetamide, N-vinyl-N-methyl-acetamide, N-vinyl-O-methylurethane as well as ethene and vinylmethyl ether, and preferably ethene, methyl vinyl ether, N-vinyl pyrrolidone, (meth)acrylamide and N-vinyl-N-methyl-acetamide.

special preference: acrylamide and vinylpyrrolidone, since they produce copolymers with particularly good solubility in water;

B = radical of maleic acid, itaconic acid or citraconic acid without any carboxylic groups special preference: maleic acid;

F = radical of a dyestuff containing one or more primary and/or secondary amino groups Y = reactive group for antigens and DNA (gene probes) with a reactive functional end group special preference: -O-$SO_2$-$CH_3$ and -O-$SO_2$-$CH_2$-$CF_3$;

X = a group which increases the solubility in water of the polymer dyestuff, especially -$SO_3H$-;

R = $C_2$-$C_{12}$-alkylene, cycloalkylene or arylene group.

Another preferred group of linkable polymer dyes has the formula:

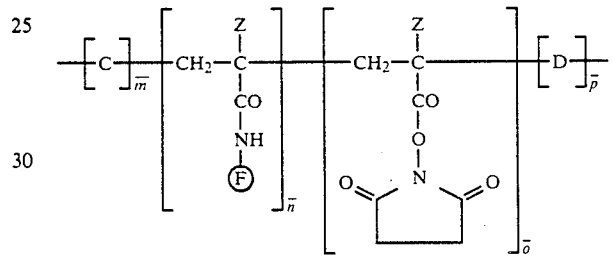

where
C = radicals of (meth)acrylamide, N-vinylpyrrolidone, N-vinyl-N-methylacetamide
special preference: (meth)-acrylamide
Z = H or $CH_3$
D = (meth) acrylic acid, 2-acryloylamino-2-methylpropane sulphonic acid, styrenesulphic acid, dialkylaminoalkyl (meth)acrylate or dialkylaminoalkyl (meth)acrylamindes or the quaternary (meth) acrylates and (meth)acrylamides obtained from these monomers.

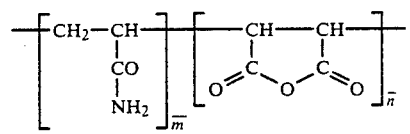

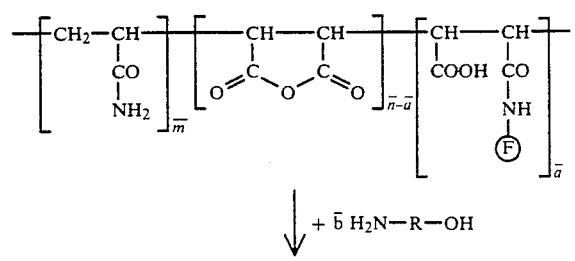

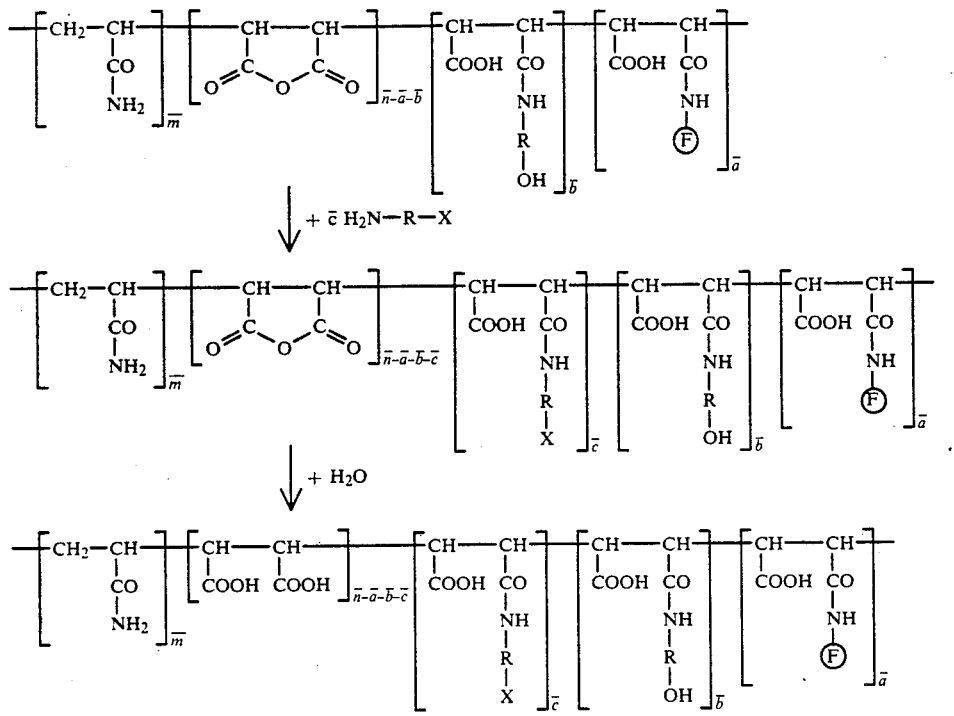

Random copolymers made from acrylamide and maleic anhydride can be produced by radical precipitation polymerization in solvents which are inert towards anhydride groups such as acetone, toluene or ethyl acetate. Copolymers with $\overline{m}=25$ to $10^4$, preferably $\overline{m}=50$ to $10^3$ copolymerized acrylamide monomers and $\overline{n}=3$ to $10^3$, preferably 5 to 200 copolymerized maleic anhydride monomers are suitable for the production of the polymer dyes according to the invention. The ratio of $\overline{m}:\overline{n}$ is normally between 2:1 and 20:1.

Ⓕ represents the dye and $\overline{a}$ represents the average number of dye molecules per polymer chain. $\overline{a}$ is between 3 and $10^3$, preferably between 5 and 500, particularly preferably between 10 and 200. $\overline{a}$ is always smaller than $\overline{n}$ by at least 1, $\overline{n}$ being the number of maleic anhydride monomers per polymer chain.

Alcohol groups are introduced into the polymer dye by reaction with an aminoalcohol $H_2-N-R-OH$. The number of these groups $\overline{b}$ per polymer chain is 1 to 5, preferably 1-3.

It is possible to carry out first either the reaction with the dye containing amino groups or the reaction with the aminoalcohol.

If desired, the remaining anhydride groups of the polymer can subsequently be reacted with an aminosulphonic acid ($-R-X=-R-SO_3H$), with an aminocarboxylic acid ($-R-X=R-COOH$) or with ammonia ($-R-X=-H$). The number $\overline{c}$ of these molecules may be equal to 0. Preferably $\overline{c}=0$ to 100. The reaction with aminosulphonic acids is particularly preferred, when the polymer dyes contain a large number of hydrophobic dye radicals per polymer chain, since the water solubility of the polymer dye is improved by virtue of the sulphonic acid groups introduced.

The reactions of the reactive base polymer (for example of the acrylamide-maleic anhydride copolymer) with the dye (F $-NH_2$), with the aminoalcohol ($H_2-N-R-OH$) and optionally with the amino acid or ammonia can be carried out in homogeneous solution or in suspension. The solvent or suspension medium should be as inert as possible towards the reactive groups of the base polymer in order to avoid harmful secondary reactions.

Preferred solvents or suspension media are those which either enable the whole reaction cycle to be carried out in homogeneous solution or which dissolve the base polymer or the polymer dye. After carrying out the reaction sequence the polymer dye is isolated in accordance with methods known per se by evaporating off the solvent, preferably by precipitating the polymer dye in a suitable organic medium.

The ratio of the bound hydrophobic dye molecules $\overline{a}$ to the number of water solubility-promoting polymer components $\overline{m}=$acrylamide and $\overline{c}=$bound aminosulphonic acid, aminocarboxylic acid or ammonia is selected in such a way that the polymer dyes have the necessary water solubility.

The separation of a possible excess of reagents can be carried out either by precipitation of the polymer dye, by repeated reprecipitation, or in the case of water-soluble reagents also by dialysis or ultrafiltration.

The purified polymer dye is subsequently dried. The linkable polymer dyes according to the invention are obtained after subsequent conversion of the alcohol groups of the polymer dye into methane sulphonyl, tresyl, trifluoroacetyl, benzene sulfphonyl, and p-toluene sulphonyl groups which can be carried out by known processes.

Analogously to acrylamide-maleic anhydride copolymers, other copolymers containing dicarboxylic anhydride groups, made from acrylamide, methacrylamide, N-$C_1$-$C_4$alkyl(meth)acrylamides, N,N-$C_1C_4$-dialkylacrylamides, N-vinylpyrrolidone, N-vinylpiperidone, N-vinylcaprolactam, N-vinylformamide, N-vinylacetamide, N-vinyl-N-methylacetamide or N-vinyl-O-methylurethane ethene or methyl vinyl ether and maleic anhydride, itaconic anhydride or citraconic anhydride can also be reacted with dyes containing amino groups, with aminoalcohols and optionally with aminosulphonic acids, aminocarboxylic acids or ammonia to form water-soluble linkable polymer dyes.

Copolymers made from acrylamide, methacrylamide, N-$C_1$-$C_4$-alkyl(meth)acrylamides, N,N-$C_1$-$C_4$-dialkylacrylamides, N-vinylpyrrolidone, N-vinylpiperidone, N-vinylcaprolactam, N-vinylformamide, N-vinylacetamide, N-vinyl-N-methylacetamide or N-vinyl-O-methylurethane and (meth)-acryloyl chloride, isocyanatoethyl methacrylate, isocyanatostyrene, isocyanatoisopropenylbenzene and vinyloxirane can be reacted analogously to the copolymers containing anhydride groups to form water-soluble linkable polymer dyes. Here, the reaction of the copolymers containing acid chloride groups are preferably carried out in the presence of tert-amines as acid acceptors.

Copolymers made from acrylamide, methacrylamide, N-$C_1C_4$alkyl(meth)acrylamides, N,N-$C_1$-$C_4$dialkylacrylamides, N-vinylpyrrolidone, N-vinylpiperidone, N-vinylcaprolactam, N-vinylformamide, N-vinylacetamide, N-vinyl-N-methylacetamide or N-vinyl-O-methylurethane and N-hydroxysuccinimide (meth)acrylate, N-hydroxyphthalimide (meth)acrylate, N-(meth)acryloylbenzotriazole or isothiocyanatophenyl (meth)acrylate can also, analogously to the copolymers containing anhydride groups, be reacted with dyes containing amino groups, with aminoalcohols and optionally with aminosulphonic acids, aminocarboxylic acids or ammonia.

However, it is additionally possible with these copolymers to only partially react the reactive groups with dyes containing amino groups and optionally with aminosulphonic acids, with aminocarboxylic acids and/or ammonia so that 1 to 5 reactive groups are left per polymer dye molecule. Linkage with the antibodies, antigens, haptens or nucleic acids then occurs via these groups.

Moreover, in these polymers hydroxyalkyl (meth)acrylates can additionally be copolymerized. In this case all acylating reactive groups can be reacted with dye molecules and optionally with the water solubility-promoting compounds and the alcohol groups can subsequently be converted into methanesulphonyl, tresyl or other reactive groups.

It is further possible to produce linkable water-soluble polymer dyes by copolymerizing dye monomers, which apart from the chromosome contain a (meth)acrylic ester or (meth)acrylamide group or some other polymerizable vinyl group or isopropenyl group with water solubility-promoting non-ionic monomer building blocks such as acrylamide, methacrylamide, N-$C_1$-$C_4$alkyl(meth)-acrylamides, N,N-$C_1$-$C_4$dialkylacrylamides, N-vinylpyrrolidone, N-vinylpiperidone, N-vinylcaprolactam, N-vinylformamide, N-vinylacetamide, N-vinyl-N-methylacetamide or N-vinyl-O-methylurethane, and with a further monomer which contains a water-resistant group which is reactive or can be activated. Here, the monomer ratios are selected in such a way that on average each polymer chain contains 1-5 groups which are reactive or can be activated and the polymer is water-soluble.

The dyes which can be used are normally those which exhibit an absorption in the ultraviolet, infrared or the visible range of the spectrum. Azo dyes, methine dyes and anthraquinone dyes are particularly suitable as dyes which absorb in the visible region, for incorporation in the polymers described. Methine dyes containing heterocycles such as oxazines, thiazines, triphendioxazines or quinophthalones are also very suitable. These dyes may be insoluble in water or may acquire water solubility by means of sulphonic acid, carboxylic acid or cationic groups.

Fluorescent dyes are preferred. Suitable dyes are for example:

Coumarins of the general formula

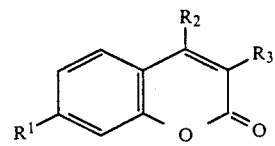

in which $R_1$ represents O-alkyl, N(alkyl)$_2$, NH-alkyl, NH-SO$_2$-alkyl NH-SO$_2$-aryl, $R_2$ represents H, CN, Cl, OH, alkylene, aryl, $R_3$ represents phenyl, hetaryl.

$R_1$ may also denote

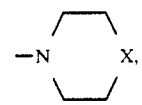

X representing O, N-alkyl or (CH$_2$)$_n$ in which n may be 0 or 1.

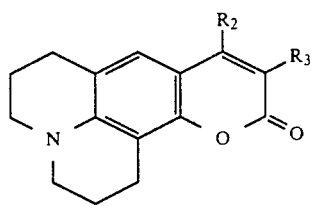

in which $R_2$ and $R_3$ have the meaning mentioned above are also very suitable.

At least one of the substituents $R_1$, $R_2$ or $R_3$ should amount to a functional group for linking the dye with the polymer. The NH$_2$ group is regarded as particularly suitable for this purpose.

Also suitable are carbostyrils of the general formula

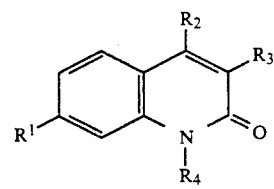

in which $R_1$, $R_2$ and $R_3$ may have the meaning given in the case of the coumarins and $R_4$ represents alkyl.

Here also, one of the substituents must bear a functional group for linking with the polymer.

Also suitable are pyrazolines of the general formula

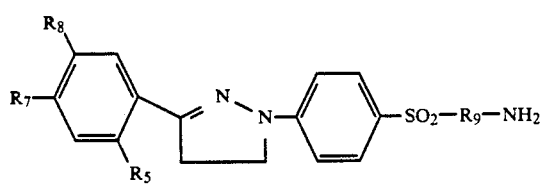

in which
R$_5$ represents H, or CH$_3$,
R$_7$ and R$_8$, independently of one another, represent H or Cl and
R$_9$ represents alkylene,

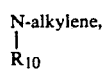

alkylene-O-alkylene
R$_{10}$ denoting alkyl.

Also very suitable are naphthalimides of the general formula

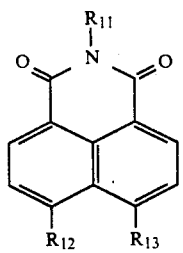

in which
R$_{11}$ represents alkyl
R$_{12}$, R$_{13}$ represent H, alkyl, N(alkyl)$_2$ and either the alkyl group at R$_{11}$ or that at R$_{12}$ or R$_{13}$ bears a NH$_2$ group for linking with the polymer.

Mentionable as also suitable are pyrenes of the general formula

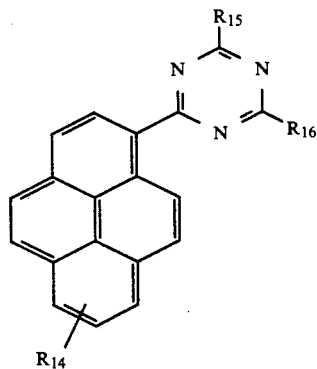

in which
R$_{14}$ represents H or SO$_3$H,
R$_{15}$ and R$_{16}$ independently of one another represent alkyl or N(alkyl)$_2$ and
an alkyl group either at R$_{15}$ or at R$_{16}$ bears and NH$_2$ group for linking with the polymer.

Also mentionable are fluoresceins of the formula

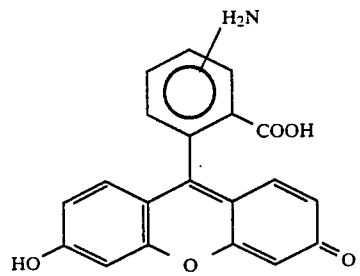

Also suitable are rhodanines of the general formula

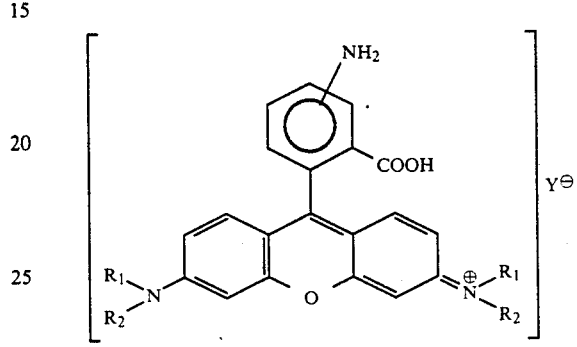

in which
Y$^\ominus$ denotes a colorless anion and
R$_1$ and R$_2$ represent alkyl,

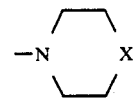

X representing O, N-alkyl or (CH$_2$)$_n$ with N=0 or 1.
R$_1$ and R$_2$ may also form a ring together with the aromatic radicals such as for example

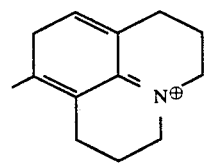

These and other dyes are from the literature such as for example "The Chemistry of Synthetic Dyes", Volume V, Academic Press (1971), or also "Fluorescent Whitening Agents", published by Georg Thieme Verlag Stuttgart (1975).

The dyes described in this invention are suitable for use as marker substances in biological analysis. For example, color or marking of antibodies or suitable functional oligonucleotides which can then be used in the usual tests (immuno-assays and gene-probe tests).

One of the main factors influencing the efficacy of such tests is sensitivity to detection. In analytical test procedures commonly used at present this is achieved by using radioactive marker substances.

However, this method has many serious drawbacks in practical use (risk of radiation, possible decomposition of the substances, special laboratory equipment required, staff need special training), and this has prevented these beneficial and efficient tests from becoming routine procedures (see e.g. WO 88-02784, Pharmacia, 21.4.88).

For this reason, much work has been carried out on replacing radioactive marking with a problem-free dyestuff marker. In this way it is possible to avoid the problems of radioactive marker substances, but the sensitivity achieved is insufficient for many analytical procedures [see e.g. Nucleic Acids Res. 16, 4957 (1988)].

The advantage of the polymer dyes described here is that they have greater sensitivity without using radioactivity.

There are many methods of linking polymer dyes with biological substrates.

1 The polymer contains suitable grafted polymer groups which are capable of reacting with antibodies or suitable functional oligonucleotides, e.g. acrylic esters of N-hydroxysuccinimide or 1-N-hydroxybenzotriazole can be incorporated by polymerization.

After loading with dye, the active polymers are reacted with the biological materials to be marked in aqueous solution. The mixtures obtained can be used for analysis either immediately or after cleaning.

2 The polymer contains suitable functional groups, which are activated in a separate chemical reaction so that they are capable of bonding with antibodies and suitable functional oligonucleotides.

Suitable groups include for example hydroxy groups which can be converted to activated esters, e.g. sulphonic acid ester or carboxylic acid ester by processes described in the literature.

In this process the dye polymer containing the hydroxyl group is converted into the mesylate in a suitable solvent, for example with methane sulphonic acid chloride.

This activated dye polymer is then reacted with the biological substrate (antibody or suitable functional oligonucleotide) in aqueous solution. The blend obtained can be used in tests either immediately or after cleaning.

Suitable functional oligonucleotides are described in the literature. These include e.g. cligonucleotides which receive functional amino, mercapto or hydroxy groups via an inert spacer.

EXAMPLE 1

Copolymers of acrylamide and maleic anhydride 57 g of acrylamide, 20 g of maleic anhydride and 0.77 g of azobisisobutyrodinitrile are dissolved in 500 ml of dry ethyl acetate and the solution is filtered. The oxygen is removed by three-fold evacuation and filling with nitrogen and the reaction mixture is stirred at 60° C. under nitrogen for 20 hours. The precipitated copolymer powder is drawn off, thoroughly washed with ethyl acetate and dried in vacuo at 50° C.

Yield: 56.3 g; N=14.8%=25% by weight of maleic anhydride,

Intrinsic viscosity $[\eta]=0.15$ (measured in 0.9% aqueous sodium chloride solution) this corresponds to an average 20 molecular weight of about 20,000 Dalton.

EXAMPLE 2

Copolymers from N-vinylpyrrolidone and maleic anhydride 26.6 g of N-vinylpyrrolidone and 23.4 g of maleic anhydride are added to 116 g of methylene chloride. The solution is freed from oxygen as in Example 1 and heated to 40° C. A solution of 250 mg of dilauroyl peroxide in 50 g of methylene chloride is added dropwise over 15 minutes and then the mixture is polymerized at 40° C. for 2 hours. The precipitated copolymer is filtered off, washed with methylene chloride and dried at 50° C. in vacuo.

Yield: 20.6 g, N=6.8%, corresponding to a molar ratio of N-vinylpyrrolidone to maleic anhydride of about 1:1; $[\eta]=0.11$ (measured in DMF).

EXAMPLE 3

Copolymers of acrylamide and acryloyloxy succinimide 54 g of acrylamide, 6 g of acryloyloxysuccinimide and 0.3 g of azobisisobutyronitrile are dissolved in 400 ml of dry ethyl acetate. The solution is freed from oxygen as in Example 1 and stirred at 60° C. under nitrogen for 20 hours. The precipitated copolymer powder is drawn off, washed thoroughly with ethyl acetate and dried at 50° C. in vacuo.

Yield: 58.4 g.

Intrinsic viscosity $[\eta]=0.71$ (measured in 0.8% aqueous sodium chloride solution) this corresponds to an average molecular weight of about 115,000 Dalton.

EXAMPLE 4

1.5 g of the acrylamide-maleic anhydride co-polymer of Example 1 are dissolved in 30 ml of dry formamide at 50° C. After cooling, 20 mg of 6-amino-1-hexanol are added at room temperature and the mixture is stirred at room temperature for 1 hour. After addition of 600 mg of 4-aminofluorescein stirring is continued at room temperature for 24 hours and subsequently at 50° C. for 5 hours. The warm mixture is precipitated in 1 l of acetone, the polymer is drawn off and dissolved in 40 ml of formamide at 50° C. After addition of 1 ml of 25% strength NH4OH solution stirring is carried out at 50° C. for 30 minutes, the mixture is cooled and freshly precipitated in 1 l of acetone. The polymer is drawn off, washed with acetone and dried at 25° C. under a high vacuum. The fluorescence is measured in water at pH 9.

Yield: 1.45 g; $\lambda_{max}=493$ nm;

Extinction at 493 nm=0.05 (4.5 mg of polymer dye in 1 l of water); Quantum yield=0.63.

1 g of the fluorescent polymer dye obtained in this way is placed in 50 ml dry pyridine at room temperature, treated with 1 g methane sulphonic acid chloride and stirred for 4 hours at room temperature under moisture-free conditions.

It is then drawn off and washed twice with 30 ml isopropanol each time.

Yield: 0.9 g weakly yellow, hygroscopic powder.

Instead of methane sulphonic acid chloride, it is possible to activate the dye in an analagous process using trifluoromethane sulphonic acid chloride, benzenesulphonic acid chloride, trifluoroacetic anhydride or p-toluenesulphonic acid chloride.

EXAMPLE 5

3 g of the acrylamide-maleic anhydride copolymer of Example 1 are dissolved in 30 ml of dry formamide at 50° C. A suspension of 266 mg of 3-(4-aminophenyl)-7-methylaminocoumarin in 2.5 ml of dry DMF is added and the mixture is stirred at 50° C. for 3 hours. 30 mg 6-amino-1-hexanol (solid) are added and the formulation is stirred for a further hour at 50° C. The solution is then added with stirring to 400 ml of ethyl acetate, the polymer being precipitated. The polymer is drawn off, intensively washed with ethyl acetate and dried over phosphorus pentoxide in vacuo.

Yield: 2.8 g; $\lambda_{max}$=389 nm;

Extinction at 389 nm=0.05 (21 mg of polymer dye in 1 l of water); Quantum yield=0.38.

1 g of the fluorescent polymer dye obtained in this way is placed in 100 ml dry pyridine and treated with 1 g methanesulphonic acid chloride. It is stirred for 4 hours at room temperature under moisture-free conditions, then drawn off and washed twice with 30 ml isopropanol each time.

Yield 0.9 g colorless, hygroscopic powder.

EXAMPLE 6

3 g of the acrylamide-acryloyloxysuccinimide copolymer of Example 3 are dissolved in 40 ml of dry formamide at 50° C. After cooling to 25° C., 0.3 g of 4-aminofluorescein are added and the mixture is stirred at 25° C. for 22 hours and at 50° C. for 4 hours. The polymer is precipitated in 500 ml of ethyl acetate, again dissolved in 30 ml of formamide and freshly precipitated in 500 ml of ethyl acetate and after isolation is dried in vacuo over phosphorus pentoxide.

Yield: 2.4 g; $\lambda_{max}$=493 nm;

Extinction at 493 nm=0.05 (12 mg of polymer dye in 1 l of water at pH 10); Quantum yield=0.18.

A corresponding acrylamide/1-acryloyloxy-benzotriazole copolymer can be with 4-aminofluorescein with similar results.

EXAMPLE 7

2.09 g of a copolymer produced according to Example 2 from maleic anhydride and N-vinylpyrrolidone are dissolved together with 1.356 g of the dye

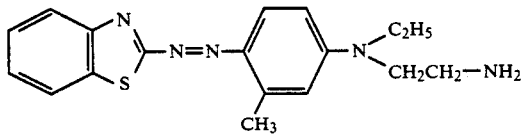

in 25 ml of formamide.

After stirring at 50° C. for 2 hours the following solution is added to the reaction mixture:

52 mg of 6-amino-1-hexanol
500 mg of 2-aminoethanesulphonic acid
5 ml of formamide
5 ml of H$_2$O Stirring is continued at 50° C. for 6 hours. The mixture is then cooled to room temperature and the resulting polymer dye is precipitated by adding it with stirring to a 15-fold excess of acetone. The filtered-off dye is dried overnight in a desicator.

Yield: 3.56 g, $\lambda_{max}$=510 nm.

Extinction at 510 nm=0.43 (40 mg of polymer dye in 1 l of H$_2$O).

EXAMPLE 8

1.5 g of the acrylamide-maleic anhydride copolymer of Example 1 are dissolved in 30 ml of dry formamide at 40°-60° C.

A solution of 115 mg (3-(4-aminophenyl)-7-diethylaminocoumarin in 1.5 ml of DMF is added and the solution is stirred at 50° C. for 1 hour. After the addition of 0.75 ml of a 1% strength 3-aminopropanol solution stirring is continued for 30 minutes and subsequently 0.5 ml of concentrated aqueous ammonia solution are added. Stirring is continued at 50° C. for 30 minutes and the mixture is added dropwise to 750 ml of ethyl acetate. The polymer dye precipitates as fine particles. It is drawn off, washed with ethyl acetate and quickly transferred to a desiccator, since it is hydroscopic. Drying is carried out at <0.1 mbar.

Yield: 1.42 g; $\lambda_{max}$=412 nm;

Extinction at 412 nm=0.07 (25 mg of polymer dye in 1 l of H$_2$O); $\lambda_{Emission}$=497 nm; Quantum yield=0.21.

EXAMPLE 9

1.5 g of the acrylamide-maleic anhydride co-polymer of Example 1 are dissolved in 30 ml of dry formamide at 50° C. After addition of a solution of 115 mg of 3-(4-aminophenyl)-7-diethylaminocoumarin in 1.5 ml DMF the mixture is stirred at 50° C. for one hour. 20 mg of 6-amino-1-hexanol (solid) are added and the mixture is stirred at 50° C. for a further 30 minutes. After addition of 300 mg of taurine (solid) the mixture is stirred at 50° C. for a further 60 minutes and the dye is subsequently precipitated, isolated and dried as in Example 8.

Yield: 1.85 g; $\lambda_{max}$=414 nm;

Extinction at 414 nm=0.07 (35 mg of polymer dye in 1 l of H$_2$O); $\lambda_{Emission}$=501 nm; Quantum yield=0.23

EXAMPLE 10

1.5 g of the acrylamide-maleic anhydride co-polymer of Example 1 are dissolved in 35 ml of dry formamide at 60° C. A solution of 300 mg of 4-amino-fluorescein in 3 ml of DMF is added and the mixture is stirred at 60° C. for 1 hour. After addition of 15 mg of 6-amino-1-hexanol (solid) the mixture is stirred at 60° C. for a further 30 minutes. 300 mg of taurine (solid) are added and stirring is continued at 60° C. for 30 minutes. Subsequently the polymer dye is isolated and dried as described in Example 1.

Yield: 1.75 g; $\lambda_{max}$=476 nm;

Extinction at 476 nm=0.04 (50 mg of polymer dye in 1 l of H$_2$O); $\lambda_{Emission}$=518 nm;

Quantum yield=0.22.

EXAMPLE 11

2.09 g of the copolymer of N-vinylpyrrolidone and maleic anhydride of Example 2 are reacted together with 131 mg of the dye 3-(4-aminophenyl)-7-diethylaminocoumarin in 6.66 g of formamide at: 50° C.

After stirring at 50° C. for 1 hour the following solution is added to the reaction mixture:

19 mg of 6-amino-1-hexanol (solid)
960 mg of an aqueous solution of Na-taurine (solids content: 43%)
3.0 g of formamide
3.0 g of water.

Stirring is continued at 50° C. for 5 hours. The mixture is then cooled to room temperature and the polymer dye is precipitated by adding the mixture with stirring to an excess of acetone. The product is dried overnight in a desiccator.

Yield: 2.40 g, $\lambda_{max}$=411 nm;

Extinction at 411 nm=0.05 (20 mg of polymer dye in 1 l H$_2$O); $\lambda_{Emission}$=550 nm;

Quantum yield=0.30.

EXAMPLE 12

5 g of the acrylamide-maleic anhydride copolymer of Example 1, 150 ml of dry formamide and 500 mg of the dye

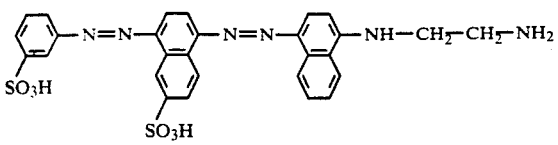

are stirred at 120° C. under nitrogen for 2 hours. After cooling to 60° C. 40 mg of 6-amino-1-hexanol (solid) are added and stirring is continued at 60° C. for one hour. 2 ml of concentrated aqueous ammonia solution are added and after a further hour at 60° C. the polymer dye is precipitated in 1.5 l of ethyl acetate and isolated as in Example 1 and dried.

Yield: 5.5 g; $\lambda_{max}=568$ nm;

Extinction at 568 nm=0.67 (0.2 mg of polymer dye in 1 ml of water).

EXAMPLE 13

1.25 g of the acrylamide-maleic anhydride copolymer of Example 1 are dissolved in 50 ml of dry formamide at 60° C. 10 mg of 6-amino-1-hexanol (solid) are added. After 1 hour at 60° C. 0.75 g of the dye

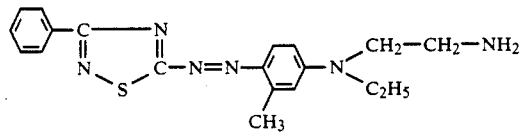

are added and the mixture is stirred at 60° C. for a further 4 hours. Then 500 mg of taurine (solid) are added and stirring is continued at 60° C. for 1 hour. The polymer dye is precipitated by adding the reaction solution dropwise to 1.5 l of acetone, and is isolated and dried as described in Example 1.

Yield: 1.75 g; $\lambda_{max}=533$ nm;

Extinction at 533 nm=0.7 (0.2 mg of polymer dye in 1 ml of water).

EXAMPLE 14

1.26 g of a random copolymer of maleic anhydride and ethylene with a molecular weight of 25,000 (EMA ®21 from Monsanto) is dissolved in 20 ml formamide. A solution of 1.695 g of a dyestuff with the following formula is added to this solution

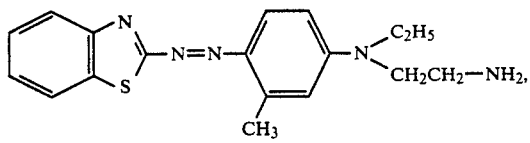

and this is also dissolved in 20 ml formamide. The reaction mixture is stirred for 1 hour at room temperature and 2 hours at 50° C. Then 117.6 mg 6-amino-1-hexanol dissolved in 5 ml formamide is added and the mixture is stirred for a further 30 minutes. Finally, 500 mg 2-aminoethanesulphonic acid is added to the reaction mixture, followed half an hour later by 5 ml H₂O and it is stirred for another 6 hours at 50° C. After cooling to room temperature the polymer dye which has formed is precipitated out by stirring in approximately 1.5 l acetone. After filtering the dye is dried in a vacuum desiccator until a constant weight is achieved.

Yield: 3.21 g; $\lambda_{max}=495$ nm;

Extinction at $\lambda_{max}=1.08$ (concentration: 40 mg/l; solvent=H₂O). Molar extinction coefficient: $1.9 \cdot 10^6$.

1 g of the polymer dye produced in this way is stirred in 50 ml dry pyridine with 1 g methanesulphonic acid chloride at room temperature for 4 hours under moisture-free conditions. It is then drawn off, washed twice with 30 ml isopropanol and dried at room temperature in an oil pump vacuum.

Yield: 0.9 g black, hygroscopic powder.

EXAMPLE 15

1.56 g of a random copolymer of maleic anhydride and methyl vinyl ether with a molecular weight of 20,000 (Gantrez ® AN 119 from GAF) is dissolved in 20 ml formamide. To this solution is added 2.034 g of a solution of the dyestuff used in Example 14 in 30 ml formamide. This is stirred for 1 hour at room temperature and 2 hours at 50° C., and then added to the following reaction mixture:

235 mg 6-amino-1-hexanol
250 mg 2-aminoethanesulphonic acid
5 ml formamide
5 ml H₂O.

After stirring for six hours at 50° C., the solution is cooled to room temperature and stirred into approximately 1.2 l ethyl acetate. The polymer dye is precipitated in the form of a fine powder, which is filtered off and then dried at room temperature in vacuo until a constant weight is obtained.

Yield: 1.25 g; $\lambda_{max}=493$ nm;

Extinction at $\lambda_{max}=0.788$ (concentration: 40 mg/l; solvent: H₂O). Molar extinction coefficient: $0.97 \cdot 10^6$.

1 g of the polymer dye produced in this way is treated with 2 g methanesulphonic acid chloride in 70 ml dry pyridine for 4 hours at room temperature in moisture-free conditions. It is then suctioned off, washed twice with 30 ml isopropanol and dried in an oil pump vacuum at room temperature.

Yield: 0.9 g black, hygroscopic powder.

EXAMPLE 16

0.5 mg monoclonal antibodies to CEA (carcinogen embryonal antigen) are incubated in 1 ml H₂O with 0.86 mg activated dye as in Example 4 for 1 hour at room temperature, dalyzed against water and lyophilized. The marked monoclonal antibodies obtained in this way are characterized by UV spectroscopy.

In immunological assays on CEA, the sensitivity obtained with these marked antibodies is greater than with analagous monomer dyes.

The CEA monoclonal antibodies can be marked in a similar way with the dyes of Examples 5, 6, 7, 9, 14, and 15.

EXAMPLE 17

500 μg of an aminolink oligonucleotide obtained from the following sequence. GCCGCCTCGG CCTCGCCGAC GCCCGGGACG GGCGCCACCC CCAACGACGT (suitable as a gene-probe test for Pseudorabies virus)[synthesis: E. Sonveaux, Bioorganic Chemistry 14, 274 (1986) and N. D. Sinha & R. M. Cook, Nucleic Acids Research 16, 2659 (1988)] is dissolved in 200 μl carbonate buffer (pH=9). An excess of a solution of a fluorescent polymer dye as in Example 6 in 300 μl formamide is added to this and it is stirred for 36 hours at room temperature. The product undergoes gel filtration with BIOARD-Bio-Gel P 4 followed by RP-HPLC cleaning.

The use of aminolink aligonucleotides produced in this way in DNA probe tests on Pseudorabies virus gives higher sensitivity than with corresponding fluorescent monomeric dyes.

The amonolink nucleotide can also be marked with activated polymer dyes as in Examples 4, 5, 7, 9, 14, and 15 and in DNA probe tests.

It is understood that the specification and examples illustrative but not limitative of the present invention and that other embodiments within the spirit and scope of the invention will suggest themselves to those skilled in the art.

We claim:

1. A polymer-bond linkable dye composition of the formula

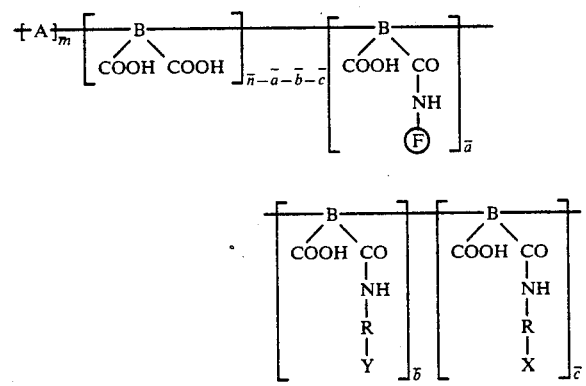

wherein

A are monomers which can be copolymerized with unsaturated dicarboxylic anhydrides, B are radicals of maleic acid, itaconic acid or citraconic acid without any carboxylic groups, F are radicals of a dyestuff containing one or more primary and/or secondary amino groups, Y are reactive groups for antigens and DNA with a reactive functional end group, X are groups which increase the solubility in water of the polymer dyestuff, R are $C_2$- to $C_{12}$-alkylene, cycloalkylene and/or arylene groups, a is between 3 to $10^3$ and smaller than $\bar{n}$, b is between 1 and 5, c is zero or between 1 and 100, m is between 25 and $10^4$, n is between 3 and $10^3$.

2. A polymer-bound linkable fluorescent dye according to claim 1, wherein the dye molecule is selected from the group consisting of a coumarin, carbostyril, pyrazoline, naphthalimide, pyrene, fluorescein or rhodanine.

3. A polymer-bound linkable dye according to claim 1, wherein the dye is selected from the group consisting of an azo dye, methine dye or anthraquinone dye.

4. A polymer-bound linkable dye according to claim 1, containing a functional group selected from the group consisting of a hydroxyl, amino, carboxyl, thio and sothiocyanate group.

5. A polymer-bound linkable dye according to claim 1, in which
   a) the water-soluble polymer backbone is an acrylamidemaleic anhydride copolymer,
   b) the dye is selected from the group consisting of a coumarin, fluorescein and rhodamine, and
   c) the functional groups are introduced by reaction with an aminoalcohol.

6. A polymer-bound linkable dye according to claim 1, in which
   a) the water-soluble polymer backbone is a vinyl pyrrolidone maleic anhydride copolymer,
   b) the dye is selected from the group consisting of a coumarin, fluorescein and rhodamine, and
   c) the functional groups are introduced by reaction with an aminoalcohol.

* * * * *

UNITED STATES PATENT AND TRADEMARK OFFICE
CERTIFICATE OF CORRECTION

PATENT NO. : 5,030,697
DATED : July 9, 1991
INVENTOR(S) : Hugl et al.

It is certified that error appears in the above-identified patent and that said Letters Patent is hereby corrected as shown below:

Col. 18, line 25  Delete " sothiocyanate " and substitute -- isothiocyanate --

Signed and Sealed this

Twenty-seventh Day of April, 1993

Attest:

MICHAEL K. KIRK

Attesting Officer

Acting Commissioner of Patents and Trademarks